United States Patent [19]

Ticker et al.

[11] 4,198,362
[45] Apr. 15, 1980

[54] METHOD AND APPARATUS FOR MOLDING AND REPLICATING MINUTE SURFACE CHARACTERISTICS

[76] Inventors: Arthur Ticker, 12117 Maddox La., Bowie, Md. 20715; Herman S. Preiser, 2 Revell Rd., Severna Park, Md. 21146

[21] Appl. No.: 947,390

[22] Filed: Oct. 2, 1978

[51] Int. Cl.² .......... B29F 5/00; B29C 1/02; G01B 5/28; G01N 19/02
[52] U.S. Cl. .......... 264/40.1; 73/104; 73/105; 264/225; 264/319
[58] Field of Search .......... 264/319, 320, 40.1, 264/225; 73/104, 105

[56] References Cited

U.S. PATENT DOCUMENTS

| 1,430,859 | 10/1922 | de Stubner. | |
|---|---|---|---|
| 2,569,195 | 9/1951 | Quetsch et al. | 264/40.1 |
| 2,601,703 | 7/1952 | Sawyer | 264/40.1 |
| 2,618,014 | 11/1952 | Sawyer et al. | 73/104 X |
| 2,886,852 | 5/1959 | Rose | 264/40.1 X |
| 3,049,752 | 8/1962 | Jorda et al. | 73/104 X |
| 3,301,046 | 1/1967 | Rubert et al. | 73/104 X |
| 3,546,130 | 12/1970 | Magdalin | 73/104 X |
| 3,862,047 | 1/1975 | Weltman et al. | 73/104 X |
| 3,966,871 | 6/1976 | Schroder | 264/40.1 X |
| 3,995,483 | 12/1976 | Hartong | 73/104 |

FOREIGN PATENT DOCUMENTS 964915 7/1964 United Kingdom ............ 73/104

*Primary Examiner*—Philip Anderson
*Attorney, Agent, or Firm*—R. S. Sciascia; Q. E. Hodges

[57] ABSTRACT

A method and apparatus for reproducing in minute detail a surface underwater. The apparatus consists of a layer of wax supported in a frame for movement into and out of contact with the surface to be reproduced, there being provided means for heating wax material to soften it and means for withdrawing the water from between the wax and surface to be molded to provide a substantially water free surface for molding.

13 Claims, 3 Drawing Figures

METHOD AND APPARATUS FOR MOLDING AND REPLICATING MINUTE SURFACE CHARACTERISTICS

The invention described herein may be manufactured and used by or for the Government of the United States of America for governmental purposes without the payment of any royalties thereon or therefor.

BACKGROUND OF THE INVENTION

It is well known to use wax to make impressions of surfaces to be later molded in other materials, such as in denistry and in the making of electrotype. The use of heat to soften the wax and use of vacuum to cause the wax to conform to the surface being molded are both broadly old in the art.

SUMMARY OF THE INVENTION

The present invention is primarily intended to reproduce in fine detail, surfaces of ships underwater so that their degree of roughness and drag may be determined. The apparatus is designed to be hand positioned by a diver and applied to selected submerged and exposed areas of a ship hull. The apparatus utilizes a vacuum and heat in a novel way to achieve the accurate reproduction of the surface of a ship hull.

DESCRIPTION OF THE PREFERRED EMBODIMENT

Figure 1A:
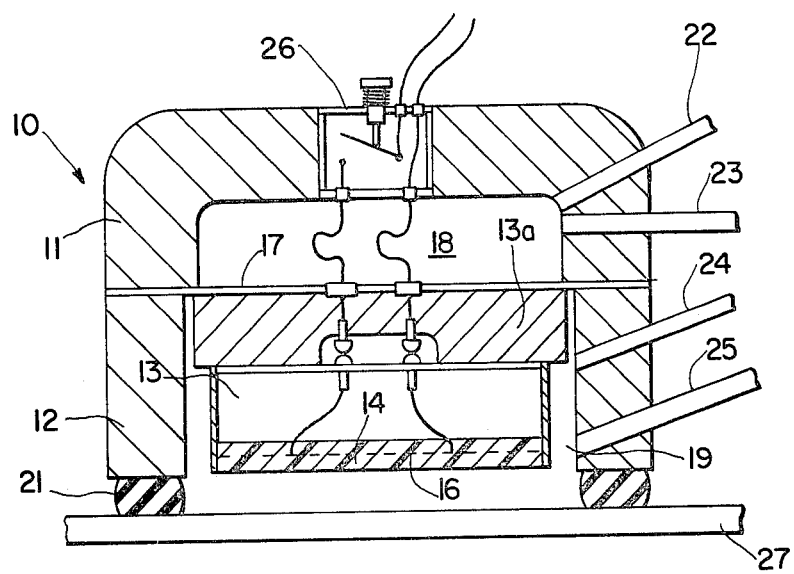
FIG. 1A is a schematic view of the invention in cross-section in it's initial position on the ship's hull.

Referring to the drawings for a more detailed description of the invention wherein corresponding parts are numbered the same, there is shown in FIG. 1A, a body 10 having upper and lower parts 11 and 12 respectively. Carried within the body 10 in sliding relation thereto is a member 13. The member 13 carries the wax or other molding material 14 which is removable and replacably, member 13 also has mounted therein a heating element 16. A piston member 13a may be connected to element 13. Separating the chamber formed by the housing 10 into two parts, subchambers 18 and 19, is a diaphram 17 which is attached between the parts 11 and 12 of the housing 10 and to the sliding element 13. Along the exposed edge of the lower housing 12 is attached a resilient gasket 21 which may be of magnetic material or constructed to function like a suction cup to facilitate attachment of the device to the ship hull 27 and to provide a watertight seal between the device and the ship hull 27.

There is provided in body 10 for each of its parts, or subchambers 18 and 19, ports 22, 23, 24 and 25 connected to suitable valving (not shown) to permit selective evacuation and flooding of the subchambers. Such valving may consist of a simple valve for each of the ports or a more complex four-way valve may be used. By proper selection of valves, air can be selectively admitted to the subchambers to aid in removing water while the subchambers are being exhausted or the subchambers can be selectively flooded.

Also a suitable switch 26 is mounted in the housing 10 and connected through a suitable electrical circuit to the electrical heating element, which for thermo plastic materials is embedded in the molding material or is mounted in close proximity to the surface of the molding material to permit the softening of the material.

Examples of such materials would be a mixture of 40% carnauba wax with 40% rosin, 10% beeswax, and 10% paraffin but other suitable waxes and some plastics, both thermo setting and thermo plastics can be used as molding materials. Also the molding material may incorporate mold release agents such as silicone oil, or may incorporate conductive metal colloids to improve heat transfer.

Figure 1B:
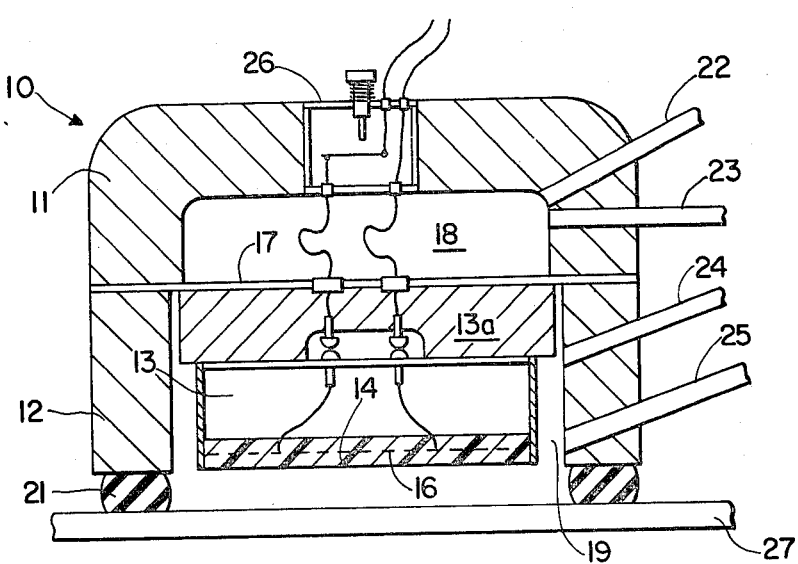
FIG. 1B is a view similar to FIG. 1A showing the heating circuit closed.
Figure 1C:
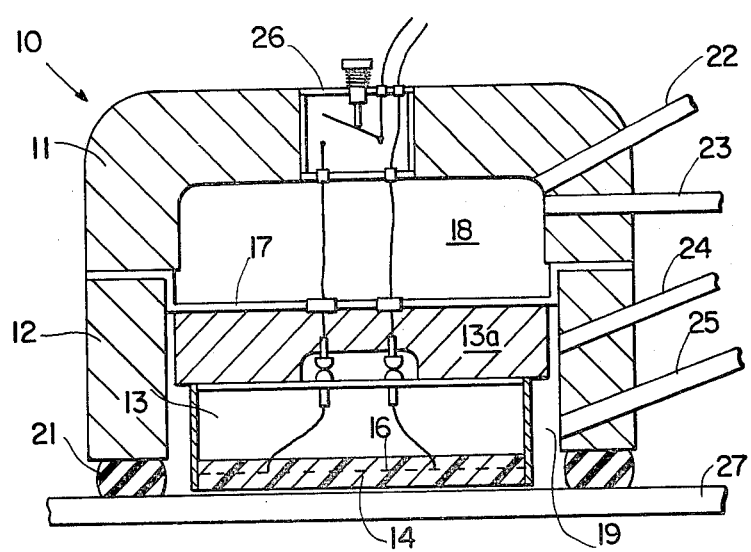
FIG. 1C is a view similar to FIG. 1A showing the elements in position for taking the impression of the surface.

As depicted in the successive drawings, the device is first positioned against a section of the hull of a ship to be replicated as is shown in FIG. 1A with the element 13 retracted from the surface. The water is then evacuated from both subchambers 18 and 19 leaving an equalized partial vacuum, as shown in FIG. 1B. Then, depending on the selected molding material, the switch 26 is then closed for sufficient time to soften, but not melt, the molding material. When the material is sufficiently soft, the switch 26 is opened to cut off the heat and then water at ambient pressure is rapidly admitted to subchamber 18, above the diaphram 17, which due to its resilience normally holds element 13 retracted from the surface being replicated. This hydrostatic pressure causes the element 13 to move into contact with and forces the molding material into molding relationship with the surface being replicated as shown in FIG. 1C. If the molding material is thermo-setting, then the switch is not closed until after the molding material has been forced against the surface. The molding material unless it is thermo-setting solidifies upon contact with the ship hull which serves as a heat sink. As a slight modification to the recited procedures, the application of heat may be delayed until the replicating material is in contact with the surface to be replicated. Such a change in operating procedure might be useful with particular replicating materials. The final step is that of readmitting water at ambient pressure to the subchamber 19. If necessary to separate the replicating material from the surface, the water in subchamber 18 can be withdrawn. The water serves to further cool any thermo plastic molding material and helps separate the replicating material from the surface.

It is to be understood that within the state-of-the-art positive replications can be made from the negatives produced by the described apparatus and method.

Obviously many modifications and variations of this invention are possible in light of the above teachings. It is therefore to be understood that within the scope of the following claims the invention may be practiced otherwise than as specifically described.

What is claimed is:

1. A method of replicating an underwater surface of a ship comprising the steps of:
   positioning a container of thermo-plastic replicating material adjacent the underwater surface to be replicated withdrawing the water from between the replicating material and the surface;
   heating the replicating material to its softening point;
   applying pressure of the ambient water to force the replicating material against the surface;
   cooling the replicating material to harden it; and withdrawing the replicating material containing the negative image of the surface from contact with the surface.

2. A method as claimed in claim 1 in which the step of withdrawing the water includes the blowing of air over the surface to complete the removal of the water.

3. An underwater replicating device comprising:
a housing for underwater attachment to a surface to be replicated;
first means within said housing for obtaining the impression of a surface being replicated;
second means for sealing said housing against the intrusion of the ambient water while the first means is applied underwater to the surface being replicated; and
means for releasing said device together with the first means from the surface.

4. A device as claimed in claim 1 which includes means within said housing to divide said housing into an upper and a lower chamber and further including means to selectively admit and remove air and water from said chambers.

5. A device as claimed in claim 4 in which said means to divide is a flexible diaphram.

6. A device as claimed in claim 5 in which said first means includes:
a container mounted on one side of said diaphram;
a removable and replaceable replicating material mounted within said container, said container being movable within said housing from a position in which said replicating material is withheld from the surface being replicated to a position in which said material contacts the surface.

7. A device as claimed in claim 6 in which said container is mounted within said lower chamber and is attached to said diaphram.

8. A device as claimed in claim 3 in which said second means comprises a deformable magnetic gasket attached to the bottom edge of said housing.

9. A device of claim 3 wherein said first means includes a wax composition as a replication material.

10. A device of claim 3 wherein said first means includes a thermo-plastic as a replicating material.

11. A device of claim 9 wherein said first means includes thermo plastic materials with additives for mold release.

12. A device of claim 3 wherein said first means includes a metallic colloid for improved heat transfer.

13. A device as claimed in claim 6 wherein a heating element is embedded in said replicating material.

* * * * *